US00PP08398P

United States Patent [19]

Guillen

[11] Patent Number: Plant 8,398

[45] Date of Patent: Sep. 28, 1993

[54] GUINEA IMPATIENS NAMED BSR-186 BONFIRE ORANGE

[75] Inventor: Mario Guillen, Cartago, Costa Rica

[73] Assignee: George J. Ball, Inc., West Chicago, Ill.

[21] Appl. No.: 917,273

[22] Filed: Jul. 23, 1992

[51] Int. Cl.[5] ..... A01H 5/00

[52] U.S. Cl. ..... Plt./87.6

[58] Field of Search ..... Plt./87.6

*Primary Examiner*—James R. Feyrer

*Attorney, Agent, or Firm*—Burns, Doane, Swecker & Mathis

[57] ABSTRACT

A new and distinct New Guinea Impatiens cultivar named BSR-186 Bonfire Orange is provided. This new cultivar was the result of a controlled breeding program wherein a plant designated N2275-1 (nonpatented in the United States) was pollinated by a plant designated N2317-1 (nonpatented in the United States). The new cultivar forms attractive orange-red blossoms combined with a strong basal branching character and a compact upright mounded growth habit and can be readily distinguished from the Ambrosia cultivar (U.S. Plant patent application pending).

1 Drawing Sheet

SUMMARY OF THE INVENTION

The present invention comprises a new and distinctive Impatiens plant, botanically known as New Guinea Impatiens, and hereafter referred to by the cultivar name BSR-186 Bonfire Orange.

The new cultivar is the product of a planned breeding program. More specifically, the breeding program which resulted in the production of the new cultivar was carried out in a controlled environment during 1988 at Linda Vista, Cartago, Costa Rica. The female parent (i.e., the seed parent) was designated N2275-1 (nonpatented in the United States) which exhibits bright orange medium-sized blossoms with green foliage. The male parent (i.e., the pollen parent) was designated N2317-1 (nonpatented in the United States) which exhibits large-sized blossoms with bronze green foliage. The parentage of the new cultivar can be summarized as follows:

N2275-1 × N2317-1.

The seeds resulting from the above pollination were sown and plantlets were obtained which were physically and biologically different from each other. Selective study resulted in the identification of a single plant of the new cultivar. This plant initially was designated BSR-186.

It was found that the cultivar of the present invention:

(a) exhibits attractive orange-red blossoms which commonly measure approximately 5.0 cm. in diameter and approximately 4.75 cm. in length,
(b) exhibits a strong basal branching character, and
(c) exhibits a compact upright mounded growth habit.

Asexual reproduction of the new cultivar by terminal or stem cuttings taken during February, 1990 at Santa Maria, Calif., U.S.A., has demonstrated that the characteristics of the new cultivar as herein described are firmly fixed and are retained through successive generations of such asexual propagation.

The BSR-186 Bonfire Orange cultivar has not been observed under all possible environmental conditions to date. Accordingly, it is possible that the phenotype may vary somewhat with variations in the environment, such as temperature, light intensity, and day length.

When the new cultivar of the present invention is compared to the Ambrosia cultivar (U.S. Plant patent application pending), it is found that the new cultivar generally exhibits smaller flowers and leaves and a more compact and more upright growth habit. The blossoms of the Ambrosia cultivar commonly measure approximately 5.5 cm. in diameter and approximately 6.0 cm. in length.

When plant material of the BSR-186 Bonfire Orange cultivar is subjected to standard random amplified polymorphic DNA marker analysis (RAPD) using polymerase chain reaction (PCR) and a known unique set of DNA primers, it is found to exhibit a different fingerprint map when compared to that of the Ambrosia cultivar which confirms its genetic distinctiveness.

Plants of the new cultivar will be marketed under the Celebration trademark by George J. Ball, Inc.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at Arroyo Grande, Calif., U.S.A.

DETAILED DESCRIPTION

The chart used in the identification of colors described herein is The R.H.S. Colour Chart of The Royal Horticultural Society, London, England. The color values were determined during the first week of January, 1992. The plants were produced from cuttings taken from stock plants and were grown at Arroyo Grande, Calif., U.S.A., under standard greenhouse conditions comparable to those used in commercial practice while utilizing a soilless growth medium and maintaining temperatures of approximately 72° F. during the day and approximately 65° F. during the night.

Propagation:

*Type cutting.*—Terminal tip.

*Time to initiate roots.*—Approximately 14 to 21 days with shorter times generally being experienced in the summer and the longer times in the winter.

*Rooting habit.*—Fibrous and branching.

Plant description:

*Form.*—Strong basal branching.

*Habit of growth.*—Compact and upright mounded. A mature plant commonly measures approximately 12 inches in height and approximately 15 inches in width.

*Foliage.*—The configuration is narrow and lanceolate. The leaves of the BSR-186 Bonfire Orange cultivar measure approximately 9.25 cm.×3.0 cm. while those of the Ambrosia cultivar measure approximately 11.65 cm.×3.25 cm. The foliage of the BSR-186 Bonfire Orange cultivar is Yellow-Green Group 147A. This can be compared to Green Group 139A for the Ambrosia cultivar. The stem color is Greyed-Purple Group 184A while that of the Ambrosia cultivar is Greyed-Purple Group 185A.

Flower description:

*Flowering habit.*—Freely flowering.

*Natural flowering season.*—Year-round in greenhouse environment.

*Flowers borne.*—Above foliage, arising from leaf axils.

*Flower color.*—Orange-Red Group 33A. This can be compared to Red Group 40A for the Ambrosia cultivar.

*Quantity of flowers.*—Approximately 5 to 10 per stem.

*Number of petals.*—Five.

*Flower diameter.*—Approximately 5.0 cm. which can be compared to approximately 5.5 cm. for the Ambrosia cultivar.

*Nectary length.*—Approximately 4.75 cm. which can be compared to approximately 6.0 cm. for the Ambrosia cultivar.

*Nectary color.*—Red Group 47B which can be compared to Red Group 46B for the Ambrosia cultivar.

*Reproductive organs.*—The anthers are fused together forming one organ that surrounds the pistil. Generally, the anthers shed pollen prior to the stigma becoming receptive. The pollen color is cream-white, White Group 155D. The stigma color is Red-Purple Color 63B and can be compared to Red-Purple Group 60A exhibited by the Ambrosia cultivar. The ovary color is Yellow-Green Group 144B and can be compared to Yellow-Green Group 146B exhibited by the Ambrosia cultivar.

I claim:

1. A new and distinct cultivar of New Guinea Impatiens named BSR-186 Bonfire Orange, substantially as herein shown and described, which:

(a) exhibits attractive orange-red blossoms which commonly measure approximately 5.0 cm. in diameter and approximately 4.75 cm. in length, (b) exhibits a strong basal branching character, and (c) exhibits a compact upright mounded growth habit.

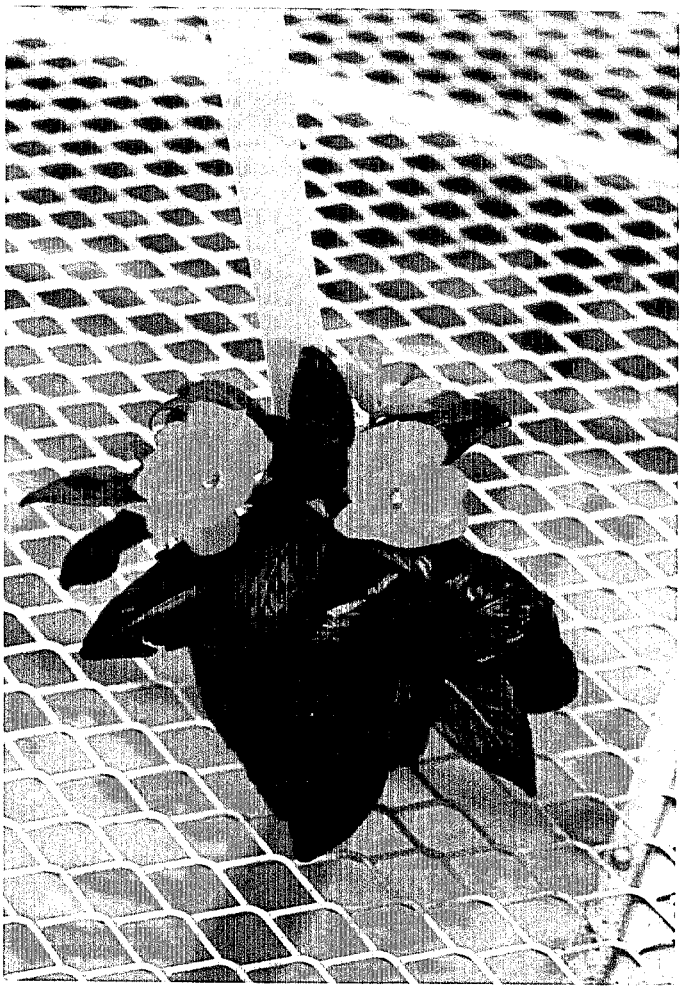

* * * * *